(12) United States Patent
Peyman

(10) Patent No.: US 6,458,141 B1
(45) Date of Patent: Oct. 1, 2002

(54) METHOD AND APPARATUS FOR CREATING A FLAP IN THE CORNEA AND INCISIONS OR SHRINKAGE UNDER THE FLAP TO CORRECT VISION DISORDERS

(76) Inventor: Gholam A. Peyman, 8654 Pontchartrain Blvd., Unit #1, New Orleans, LA (US) 70124

( * ) Notice: Subject to any disclaimer, the term of this patent is extended or adjusted under 35 U.S.C. 154(b) by 0 days.

(21) Appl. No.: 09/522,901

(22) Filed: Mar. 10, 2000

(51) Int. Cl.⁷ .................................................. A61F 9/00
(52) U.S. Cl. ...................................... 606/166; 606/167
(58) Field of Search ........................... 606/1, 166, 167, 606/5, 4, 17, 161, 170, 180

(56) References Cited

U.S. PATENT DOCUMENTS

| | | | |
|---|---|---|---|
| 4,298,004 A | | 11/1981 | Schachar et al. ............ 128/305 |
| 4,807,623 A | * | 2/1989 | Lieberman et al. .......... 606/166 |
| 4,903,695 A | | 2/1990 | Warner et al. ................. 606/4 |
| 5,215,104 A | | 6/1993 | Steinert ....................... 128/898 |
| 5,591,185 A | * | 1/1997 | Kilmer et al. ............... 606/166 |
| 5,722,971 A | | 3/1998 | Peyman ......................... 606/5 |
| 5,833,701 A | * | 11/1998 | Gordon ........................ 606/166 |
| 5,919,185 A | | 7/1999 | Peyman ......................... 606/5 |
| 5,935,140 A | * | 8/1999 | Buratto ........................ 606/166 |
| 5,964,748 A | | 10/1999 | Peyman ........................ 606/17 |

* cited by examiner

Primary Examiner—Gary Jackson
(74) Attorney, Agent, or Firm—Roylance, Abrams, Berdo & Goodman, L.L.P.

(57) ABSTRACT

An apparatus and method for precisely forming a flap in the live cornea about at least a portion of the circumference of the live cornea, and then, if desired, forming incisions or tissue shrinkage in the live cornea under the flap without removing or ablating any tissue, and without damaging the Bowman's layer, to correct vision disorders in the eye such as astigmatism, myopia, hypertrophic, hyperopia and presbyopia, to name a few. The apparatus and method employ a stabilizing device and a cutting tool. The stabilizing device is adapted to be attached to the front surface of a live cornea to apply suction to the live cornea which prevents the live cornea from moving when the cutting is being performed. The cutting tool can be, for example, a blade, water jet, laser, or any combination thereof, that is directed toward the cornea that is stabilized in the stabilizing device to cut the flap in the cornea, which can be through the front surface of the cornea about at least a portion of the periphery of the cornea, or can be through the front surface of the cornea is a manner similar to the LASIK procedure described above. The blade or laser can further be used to cut differently-shaped incisions under the flap, such as radial incisions, actuate incisions, and so on, as desired, to correct the vision disorder. Also, tools such as a laser, diathermy device, or microwave emitting device can be used, as desired, to create shrinkage under the flap without ablating the tissue or removing any tissue, to further correct vision disorders.

20 Claims, 14 Drawing Sheets

METHOD AND APPARATUS FOR CREATING A FLAP IN THE CORNEA AND INCISIONS OR SHRINKAGE UNDER THE FLAP TO CORRECT VISION DISORDERS

BACKGROUND OF THE INVENTION

1. Field of the Invention

The present invention relates to a method and apparatus for creating a flap in a live cornea of an eye and creating incisions or shrinkage under the flap, as appropriate, to correct vision disorders without damaging the Bowman's layer of the eye. More particularly, the present invention relates to an apparatus and method employing a cutting tool, such as a blade, water jet or laser, that can be directed to cut a flap in a live cornea, along with incisions or shrinkage under the flap, as appropriate, to correct vision disorders such as astigmatism, myopia, hyperopia or presbyopia, when the flap is allowed to relax back onto the remainder of the cornea and the incisions and shrinkage areas are permitted to heal.

2. Description of the Related Art

A normal ametropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypertrophic or hyperopia, astigmatism and presbyopia.

A myopic eye has either an axial length that is longer than that of a normal ametropic eye, or a cornea or lens having a refractive power stronger than that of the cornea and lens of an ametropic eye. This stronger refractive power causes the far point to be projected in front of the retina.

Conversely, a hypermetropic or hyperopic eye has an axial lens shorter than that of a normal ametropic eye, or a lens or cornea having a refractive power less than that of a lens and cornea of an ametropic eye. This lesser refractive power causes the far point to be focused on the back of the retina.

An eye suffering from astigmatism has a defect in the lens or shape of the cornea. Therefore, an astigmatic eye is incapable of sharply focusing images on the retina.

In order to compensate for the above deficiencies, optical methods have been developed which involve the placement of lenses in front of the eye (for example, in the form of glasses or contact lenses). However, this technique is often ineffective in correcting severe vision disorders.

An alternative technique is surgery. For example, in a technique known as myopic keratomileucis, a microkeratome is used to cut away a portion of the front of the live cornea from the main section of the live cornea. That cut portion of the cornea is then frozen and placed in a cyrolathe where it is cut and reshaped. Altering the shape of the cut portion of the cornea changes the refractive power of this cut portion, which thus effects the location at which light entering the cut portion of the cornea is focused. The reshaped cut portion of the cornea is then reattached to the main portion of the live cornea. Hence, this reshaped cornea will change the position at which the light entering the eye through the cut portion is focused, so that the light is focused more precisely on the retina, thus remedying the ametropic condition.

Keratophakia is another known surgical technique for correcting severe ametropic conditions of the eye by altering the shape of the eye's cornea. In this technique, an artificial organic or synthetic lens is implanted inside the cornea to thereby alter the shape of the cornea and thus change its refractive power. Accordingly, as with the myopic keratomileucis technique, it is desirable that the shape of the cornea be altered to a degree which enables light entering the eye to be focused correctly on the retina.

A further known surgical technique is radial keratotomy. This technique involves cutting numerous slits in the front surface of the cornea to alter the shape of the cornea and thus, alter the refractive power of the cornea. It is desirable that the altered shape of the cornea enables light entering the eye to be focused correctly on the retina. However, this technique generally causes severe damage to the Bowman's layer of the cornea, which results in scarring. This damage and scarring results in glare that is experienced by the patient, and also creates a general instability of the cornea. Accordingly, this technique has generally been abandoned by most practitioners.

Laser in situ keratomileusis (LASIK), as described, for example, in U.S. Pat. No. 4,840,175 to Peyman, the entire contents of which is incorporated herein by reference, is a further known surgical technique for correcting severe ametropic conditions of the eye by altering the shape of the eye's cornea. In the LASIK technique, a motorized blade is used to separate a thin layer of the front of the cornea from the remainder of the cornea in the form of a flap. The flap portion of the cornea is lifted to expose an inner surface of the cornea. The exposed inner surface of the cornea is irradiated with laser light, ablated and thus reshaped by the laser light. The flap portion of the cornea is then repositioned over the reshaped portion and allowed to heal.

In the LASIK technique, it is critical that the tissue ablation is made with an excimer laser, which is difficult to operate and is very expensive. In addition. the process requires tissue removal which might lead to thinning of the cornea or ectasia, which is abnormal bulging of the cornea that can adversely affect vision.

In all of the above techniques, it is necessary that the cornea be prevented from moving while the cutting or separating of the corneal layers is being performed. Also, it is necessary to flatten out the front portion of the cornea when the corneal layers are being separated or cut so that the separation or cut between the layers can be made at a uniform distance from the front surface of the cornea. Previous techniques for flatting out the front surface of the cornea involve applying pressure to the front surface of the cornea with an instrument such as a flat plate.

In addition to stabilizing the cornea when the cutting or separating is being performed, the cutting tool must be accurately guided to the exact area at which the cornea is to be cut. Also, the cutting tool must be capable of separating layers of the cornea without damaging those layers or the surrounding layers.

Furthermore, when the keratotomy technique is being performed, it is desirable to separate the front layer from the live cornea so that the front layer becomes a flap-like layer that is pivotally attached to the remainder of the cornea and which can be pivoted to expose an interior layer of the live cornea on which the implant can be positioned or which can be ablated by the laser. However, these methods disturb the optical axis of the eye, which passes through the center of the front-portion of the cornea and extends longitudinally through the eye. Care also must be taken so as not to damage the Bowman's layer of the eye.

In addition, because the epithelium cells which are present on the surface of the live cornea may become attached to the blade when the blade is being inserted into the live cornea and thus become lodged between the layers of the live cornea, thereby clouding the vision of the eye, it is desirable to remove the epithelium cells prior to performing the cutting.

Examples of known apparatuses for cutting incisions in the cornea and modifying the shape of the cornea are described in U.S. Pat. No. 5,964,776 to Peyman, U.S. Pat. No. 5,919,185 to Peyman, U.S. Pat. No. 5,722,971 to Peyman, U.S. Pat. No. 4,298,004 to Schachar et al., U.S. Pat. No. 5,215,104 to Steinert, and U.S. Pat. No. 4,903,695 to Warner.

A need exists for an improved apparatus and method for cutting a flap and, if appropriate, one or more incisions in a live cornea to correct vision disorders. Specifically, a need exists for an improved apparatus and method which corrects vision disorders without ablating or removing tissue from the cornea, without placing an insert in the cornea and, most importantly, without damaging the Bowman's layer.

SUMMARY OF THE INVENTION

An object of the present invention is to provide an apparatus and method for precisely forming a flap in a live cornea and then, if desired, forming incisions and tissue shrinkage in the live cornea under the flap without ablating or removing tissue from the cornea, or implanting any material in the cornea, to correct vision disorders in the eye.

Another object of the present invention is to provide an apparatus and method for precisely forming a flap in a live cornea without disturbing the optical axis or Bowman's layer of the eye.

A further object of the present invention is to provide an apparatus and method for precisely forming a flap in the live cornea about at least a portion of the circumference of the live cornea, and then, if desired, forming incisions or tissue shrinkage in the live cornea under the flap without removing or ablating any tissue, to correct vision disorders in the eye such as astigmatism, myopia, hypertrophic, hyperopia and presbyopia, to name a few.

This and other objects of the present invention are substantially achieved by an apparatus and method for forming a flap in a live cornea of any eye to correct vision disorders in the eye such as astigmatism, myopia, hypertrophic, hyperopia and presbyopia. The apparatus and method employ a stabilizing device and a cutting tool. The stabilizing device is adapted to be attached to the front surface of a live cornea to apply suction to the live cornea which prevents the live cornea from moving when the cutting is being performed. The stabilizing device includes a transparent or substantially transparent viewer through which the front surface of the cornea to which the suction is being applied can be viewed. The suction pulls the front surface of the cornea in a direction toward the viewer so that the front surface of the cornea contacts a bottom surface of the viewer and thus flattens out against that bottom surface. The cutting tool can be, for example, a blade, water jet, laser, or any combination thereof, that is directed toward the cornea that is stabilized in the stabilizing device to cut the flap in the cornea, which can be through the front surface of the cornea about at least a portion of the periphery of the cornea, or can be through the front surface of the cornea is a manner similar to the LASIK procedure described above. Any of the cutting tools can further be used to cut differently-shaped incisions under the flap, such as radial incisions, actuate incisions, and so on, as desired, to correct the vision disorder. Tools such as a laser, diathermy device, or microwave emitting device can be used, as desired, to create shrinkage under the flap without ablating the tissue or removing any tissue, to further correct vision disorders.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which.

DETAILED DESCRIPTION OF THE PREFERRED EMBODIMENTS

An embodiment of an apparatus 100 for creating a substantially circular flap about the circumference of a live cornea of an eye 102 is illustrated in FIGS. 1–5. Specifically, the apparatus 100 includes a cornea holding apparatus 104 and a cutting mechanism 106.

Figure 1:
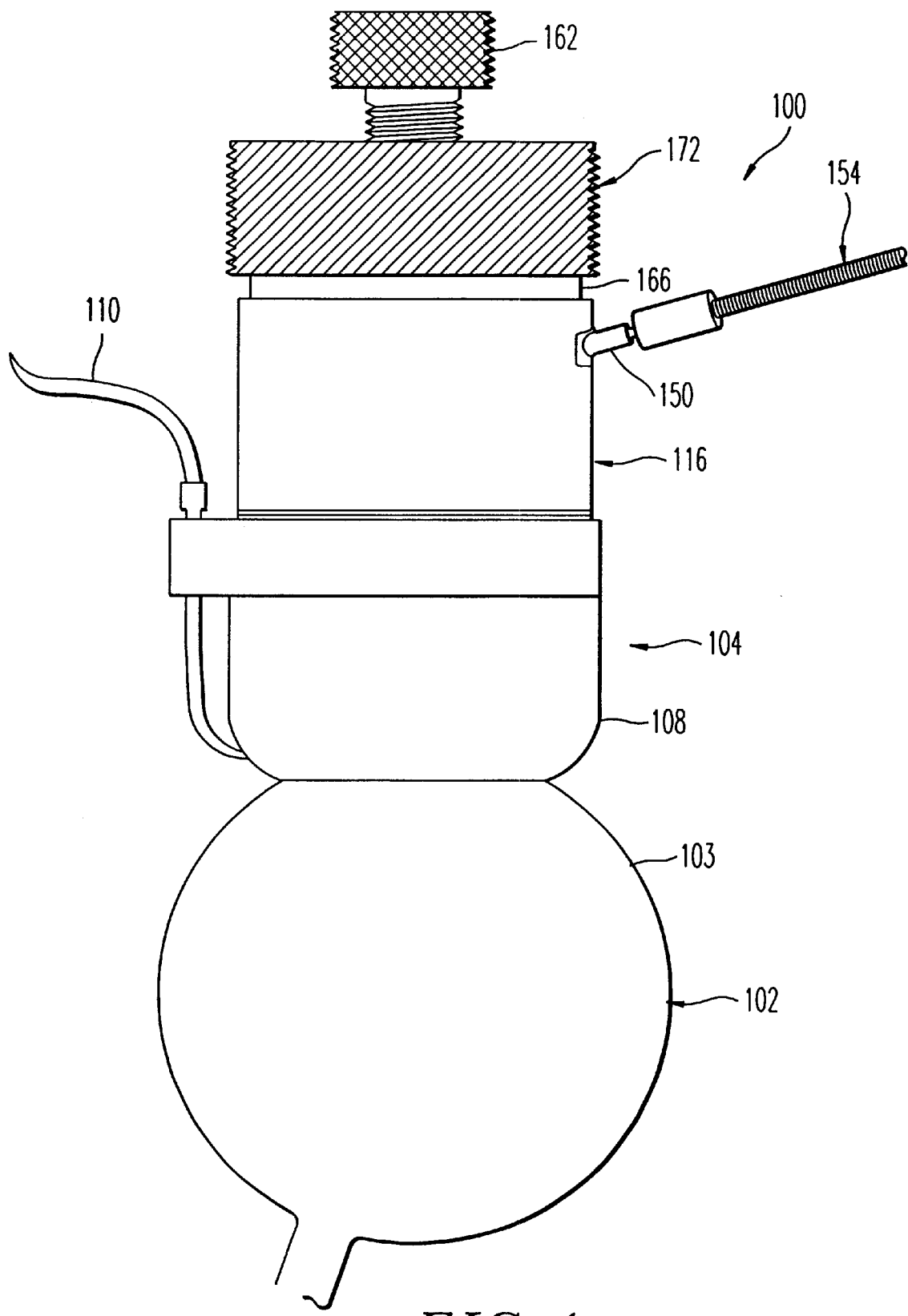
FIG. 1 is a side view of an apparatus for creating a flap in a live cornea of an eye according to an embodiment of the present invention.
Figure 2:
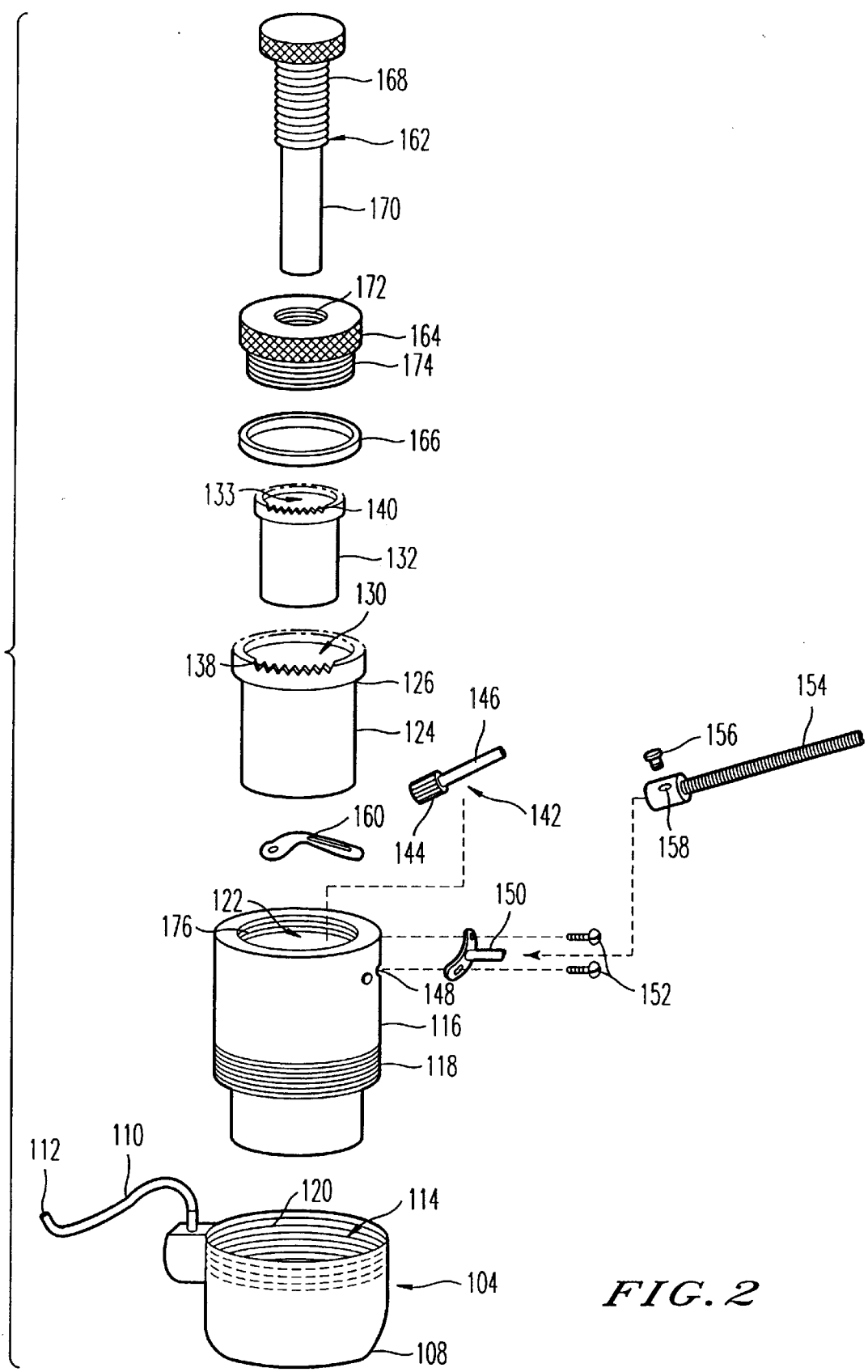
FIG. 2 is an exploded perspective view of the apparatus shown in FIG. 1.
Figure 3:
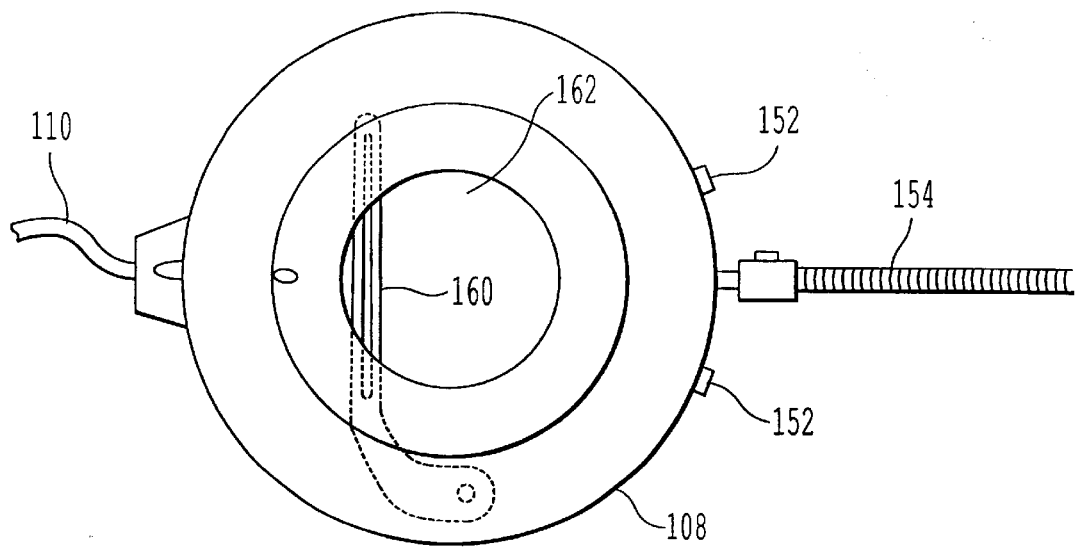
FIG. 3 is a bottom view of the apparatus shown in FIG. 1.
Figure 4:
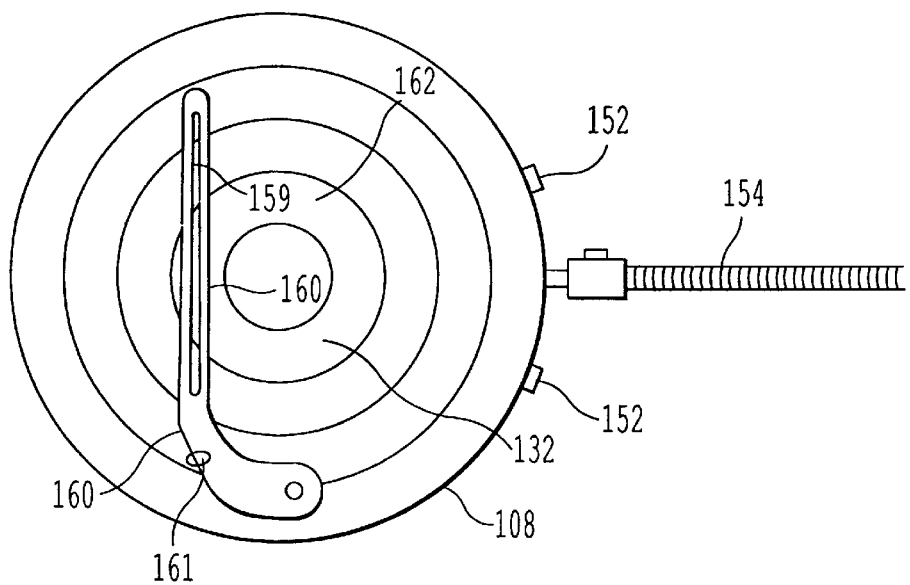
FIG. 4 is a bottom view of the apparatus shown in FIG. 1 with the cornea stabilizing device removed.
Figure 5:
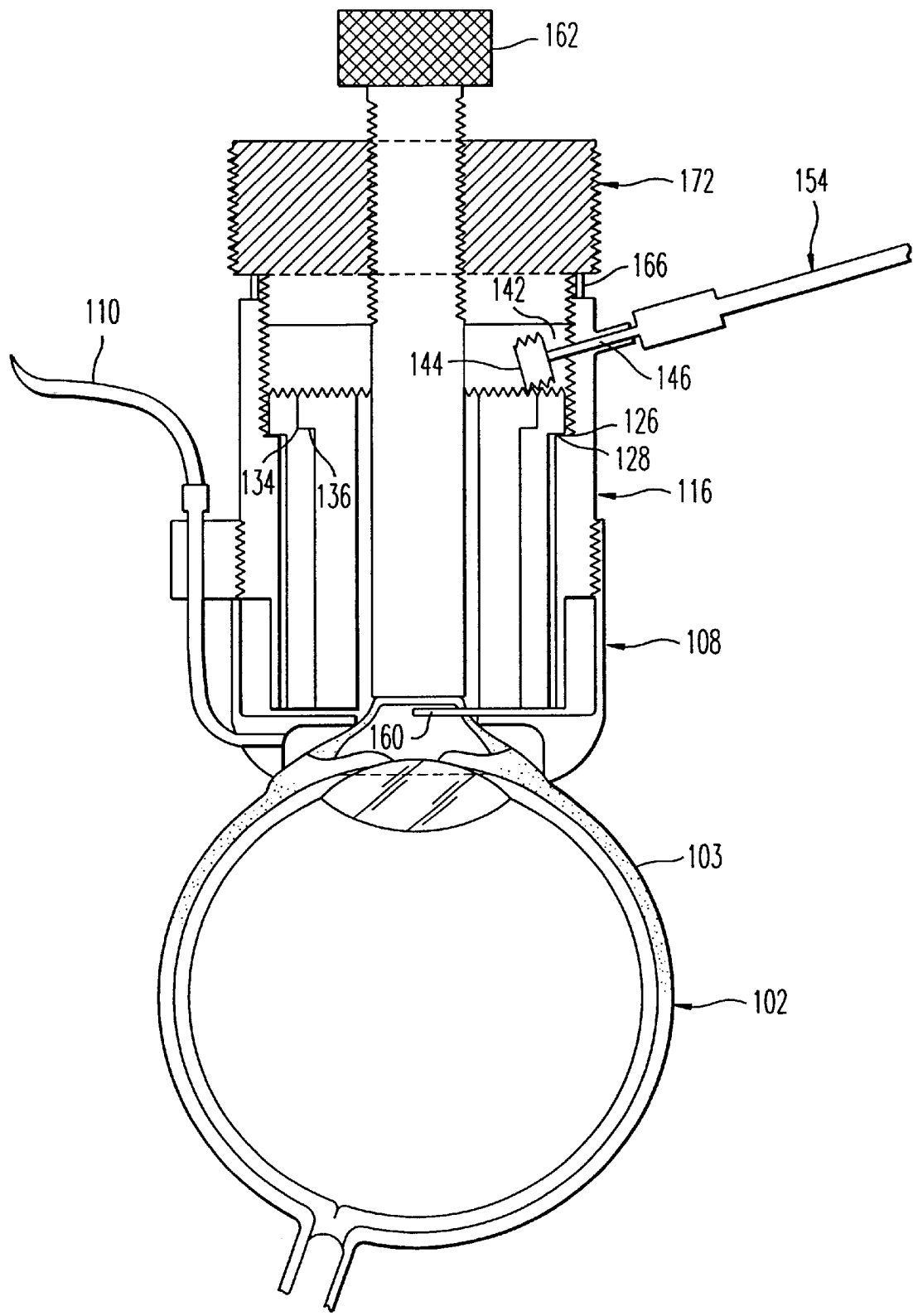
FIG. 5 is a cross-sectional view of the apparatus and eye as shown in FIG. 1.

The cornea holding apparatus 104 includes a cornea receiving section 108 which receives a front portion of a live cornea 103 of a patient's eye 102 as shown, for example, in FIG. 1. Specifically, a tube 110 having an opening 112 therein extending along the length thereof is coupled to the cornea receiving section 108 such that the opening 112 communicates with an interior cavity 114 of the cornea receiving section 108. The interior surface of the cornea receiving section 108 can include a plurality of steps or ridges (not shown) which contact the surface of the live cornea 103 and assist in stabilizing the cornea from movement when the cornea is received in the cornea receiving section 108. That is, as the front surface of the cornea 103 of the eye 102 is received in the receiving section 108, suction will be applied via tube 110 to the internal cavity 114 of the receiving section 108 to suck the cornea into the cavity 114.

As further illustrated, the cutting mechanism 106 includes a cylindrical housing 116 having threads 118 that engage with threads 120 in the inner surface of the cornea holding apparatus 104 to secure the cutting mechanism 106 to the cornea holding apparatus 104. The cylindrical housing 116 includes an opening 122 therein which receives a large cylindrical member 124 having a flange portion 126 that rests on a step 128 in the interior of the cylindrical housing 116.

The large cylindrical member 124 has an opening 130 passing therethrough, into which is received a small cylindrical member 132. The small cylindrical member 132 has a flange portion 134 that rests on a step 136 in the interior of the large cylindrical member 124. Accordingly, the small cylindrical member 132 becomes nested within the large cylindrical member 124. Also, the large and small cylindrical members 124 and 132 remain rotatable with respect to each other and with respect to the cylindrical housing 116.

As further shown, the large cylindrical member 124 includes teeth 138 about its upper circumference, and the small cylindrical member 132 includes teeth 140 about its upper circumference. A gear member 142 includes a gear portion 144 that engages with the teeth 138 and 140 of the large and small cylindrical members 124 and 132, respectively. Gear member 142 further includes a shaft portion 146 that passes through an opening 148 in the cylindrical housing 116 and further through an opening in a support 150 that is screwed to the cylindrical housing 116 by screws 152.

The shaft portion 146 is further received into an opening in a drive shaft 154 which can be manually or mechanically rotated to rotate the gear member 142 as described in more detail below. The shaft portion 146 is secured to the drive shaft 154 by a screw 156 that passes through a hole 158 in the drive shaft 154 and engages with the shaft portion 146 to secure the shaft portion 146 to the drive shaft 154. A blade 160 made of an appropriate material such as surgical steel and having a diamond cutting edge, for example, is coupled to the bottoms of large cylindrical member 124 and small cylindrical member 132 by clips 159 and 161, and is thus rotated when the large and small cylindrical members 124 and 132 are rotated by the gear member 142 as described in more detail below.

The cutting mechanism 106 further includes a clear or substantially clear viewer 162, a viewer mounting portion 164, and a spacer 166. The viewer 162 is preferably a synthetic material, such as an acrylic, plexy glass, or the like, having threads which are as fine as possible. The viewer 162 includes a threaded portion 168 and a shaft portion 170. The shaft portion 170 passes through a threaded opening 172 in the viewer mounting portion 164 so that the threaded portion 168 engaged with the threads in the threaded opening 172. The shaft portion 170 further passes through the opening 133 of small cylindrical member 132, such that the bottom of shaft portion 170 extends toward the bottom of small cylindrical member 132.

The viewer mounting portion 164 further includes threads 174 that engage with threads 176 in the cylindrical housing 116 to secure the viewer mounting portion 164 with the housing 116. Spacer 166 limits the depth to which the viewer mounting portion 164 is received in housing 116. Furthermore, the threaded engagement between threaded opening 172 and threaded portion 168 of the viewer 162 enable the bottom of the shaft portion 170 of the viewer to be raised or lowered as desired by rotating the viewer 162 clockwise or counterclockwise.

Figure 6:
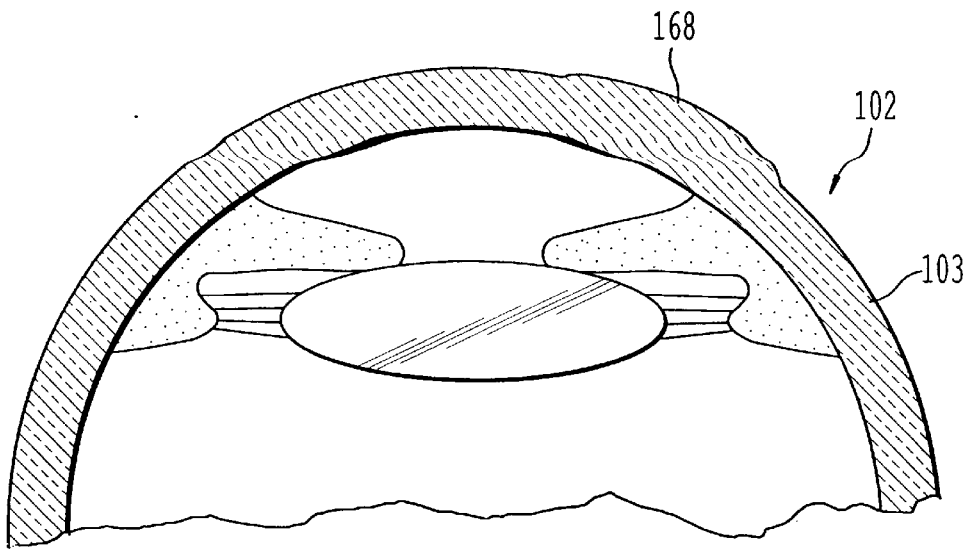
FIG. 6 is a cross-sectional view of an eye having an astigmatic portion.

A manner in which the apparatus 100 discussed above is used to correct vision disorders in the eye 102 will now be described. FIG. 6 is a cross section of an eye 102 suffering from astigmatism. Specifically, the front surface of the cornea 103 of the eye 102 has an astigmatic portion 178. The astigmatic portion 178 is a portion of the cornea 103 that is bulged or otherwise misshaped with respect to the remaining front surface of the cornea 103. The apparatus 100 can be used to cut a flap into at least the astigmatic portion 178 of the cornea 103 to correct the astigmatic condition.

The thickness of the cornea 103 is first measured. Then, the front of the eye 102 is placed in the receiving section 108 of the cornea holding apparatus 104 as shown, for example, in FIGS. 1 and 5. A vacuum is applied to tube 110 to create a suction in the cornea receiving section 108 which draws the front of the cornea of the eye 102 toward the bottom of the viewer 162 so that the bottom surface of the viewer 162 flattens the front surface of the cornea as shown, in particular, in FIG. 5. The position of the bottom of the viewer 162 can be adjusted in a manner described above so that when the front portion of the cornea contacts the bottom of the viewer 162, the astigmatic portion 178 of the cornea 103 is aligned with the blade 160.

Figure 7:
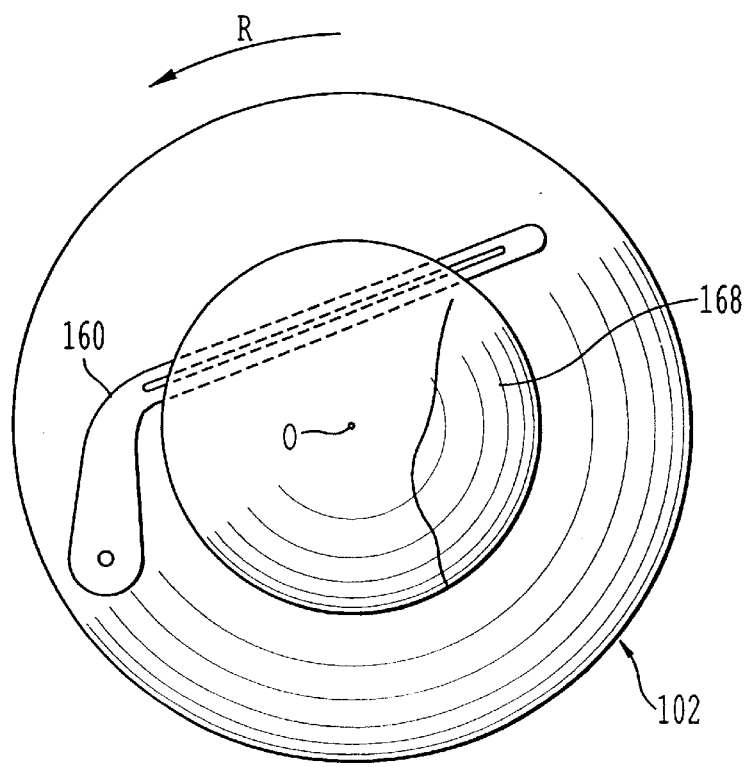
FIG. 7 is a top view of the eye shown in FIG. 6 into which an incision is being formed by the apparatus shown in FIGS. 1–5.
Figure 8:
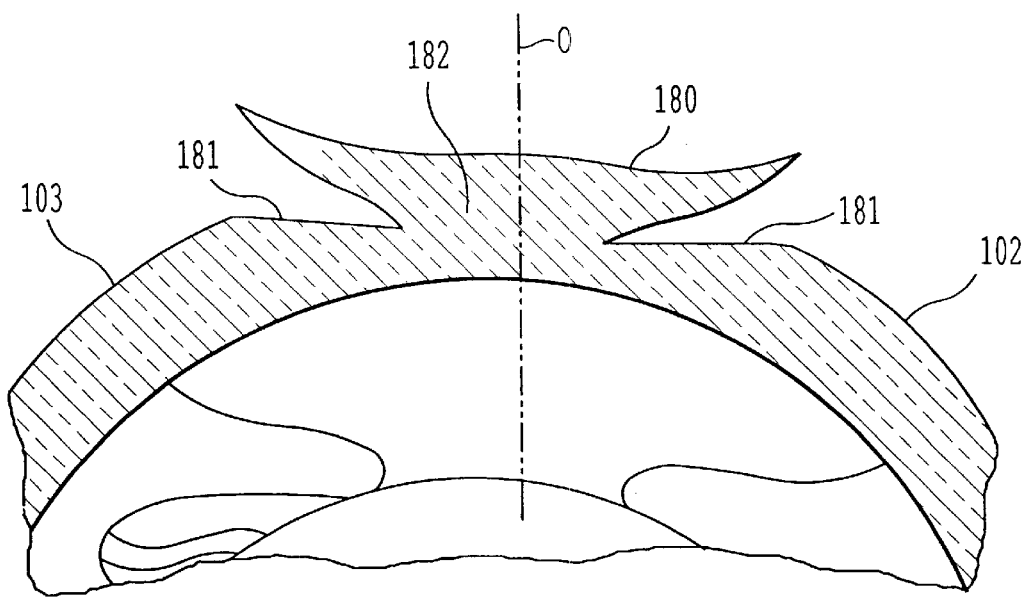
FIG. 8 is a cross-sectional view of the eye shown in FIG. 6 having a flap formed by the apparatus shown in FIGS. 1–5.

The drive shaft 154 of the cutting mechanism 106 can then be rotated to cut an incision in the cornea of the eye 102 to correct the vision disorder of the eye. For example, as shown in FIGS. 7 and 8, when the drive shaft 154 is rotated, the gear member 142 engages the teeth 138 and 142 of the large and small cylindrical members 124 and 132, respectively, and rotates the large and small cylindrical members 124 and 132. When the large and small cylindrical members 124 and 132 rotate. they move the blade 160 about the circumference of the cornea 103 in a direction along arrow R in FIG. 7 to create an incision in the cornea 103. The drive shaft 154 can be rotated to cause the blade 160 to create an incision only in the astigmatic portion 178 of the cornea 103, or about the entire circumference of a cornea 103 or any portion of the circumference of the cornea 103.

Assuming, for example, that the drive shaft 154 is rotated to rotate the blade 160 about the entire circumference of the cornea 103, the incision in the cornea 103 forms a flap 180 that is separable from the remainder of the cornea 103 about the perimeter of the cornea 103 to expose an exposed surface 181 of the cornea 103, but remains attached at the central portion 182 of the cornea 103 as shown. Hence, the incision does not alter the optical axis O of the eye 102. The flap 180 can have a uniform thickness, or a varying thickness, as desired, and can have an outer diameter from about 5 mm to about 10 mm, or any other suitable dimension. The central portion can have an outer diameter of as little as about 0.5 mm or as large as 7 mm, or any other suitable dimension.

After the flap 180 has been created as described above, the suction force is discontinued, and the eye 102 can be removed from the cornea holding apparatus 104. The thickness of the exposed surface 181 can then be measured and, if appropriate, further incisions in the exposed surface 181 can be made in the manners discussed in detail below. The flap 180 can then be repositioned back onto the exposed surface 181 and the remaining portion of the cornea 103 as shown, for example, in FIG. 9, and permitted to assume a relaxed position. It is important to note that the incision forming the flap 180 relaxes the Bowman's layer of the cornea 103 to therefore change the curvature of the cornea 103 to thus correct the vision disorder in the manner described above.

The underside of the flap 180 and the exposed surface 181 of the cornea 103 can be washed with a suitable solution to remove debris from underneath the flap 180 and on the exposed surface 181. Furthermore, antibiotic drops containing an anti-infection agent can be placed on the exposed surface 181 and on the underside of the flap 180.

Figure 9:
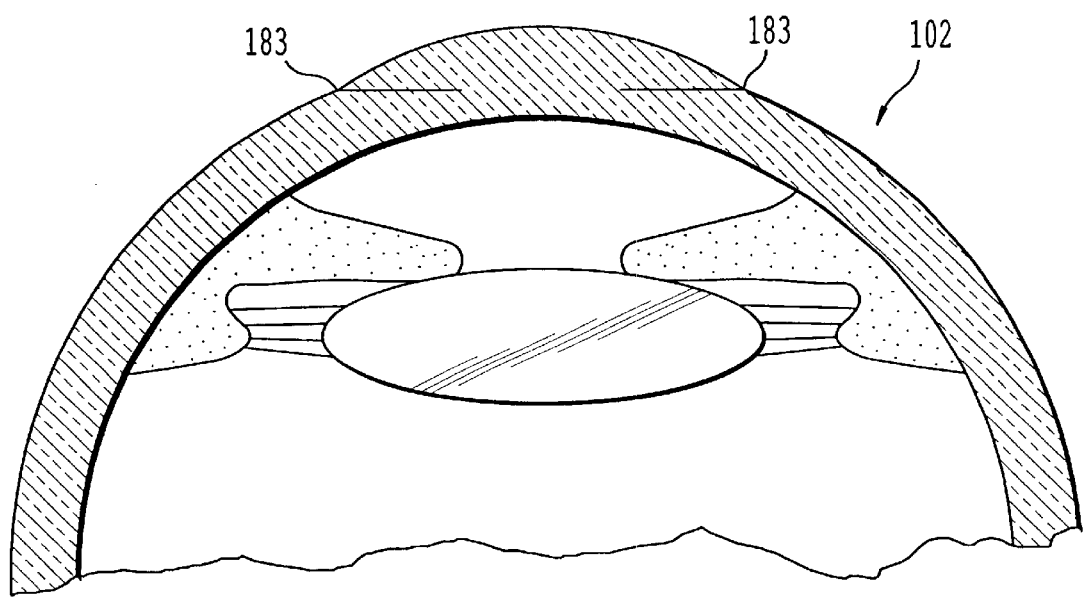
FIG. 9 is a cross-sectional view of the eye shown in FIGS. 6 and 9 with the flap replaced.

As indicated in FIG. 9, the edge 183 of the flap 180 can overlap a portion of the cornea 103 when the flap 180 assumes its relaxed state. In addition, if desired, an adhesive material such as syanocrylate (commonly referred to "Derma Bond" made by Ethicon Co.), or other adhesives such as polyethylene glycol hydrogels manufactured by Sharewater Polymers, Inc. or Cohesion Technologies, Inc., or Advaseal made by Focalseal, Inc., can be used to secure the flap in place during healing. Also, a short-term bandage can be attached to the front of the eye, or a punctal plug can be inserted to inhibit drainage or tear flow. The incision forming the flap 180 can then be permitted to heal for the appropriate length of time.

Figure 10:
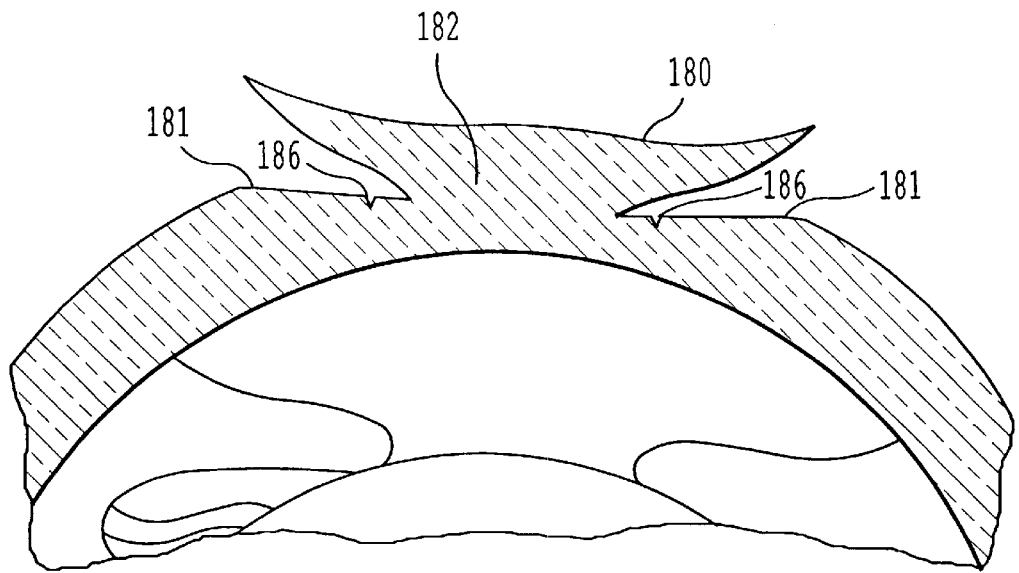
FIG. 10 is a cross-sectional view of the eye shown in FIG. 6 with a flap formed as shown in FIG. 9 and additional incisions under the flap.

In addition to the process described above, further incisions or tissue shrinkage can be made in the cornea underneath the flap 180 before the flap 180 is repositioned over the exposed surface 181 to correct other vision disorders such as myopia, hyperopia or presbyopia. For example, as shown in FIG. 10, the flap 180 can be created by blade 160 of the apparatus 100 as described above, and lifted from the remaining portion of the cornea 103.

As described in more detail below, the incision creating the flap 180 can alternatively be made by a cutting tool, such as a keratome or scalpel, a razor blade, a diamond knife, a contact (fiber optic) laser, a non-contact laser having nano-second ($10^{-9}$), pico-second ($10^{-12}$) or femto-second ($10^{-15}$) pulses, or water-jet cutting tool as manufactured, for example, by Visijet Company. The contact or non-contact laser can emit their radiation within the infrared, visible or ultraviolet wavelength. A cutting tool such as a scalpel, a razor blade, a diamond knife, a contact (fiber optic) laser or a non-contact laser having nano-second ($10^{-9}$), pico-second ($10^{-12}$) or femto-second ($10^{-15}$) pulses at the wavelengths described above can be used to create additional incisions 186 in the exposed surface 181. It is noted that the above lasers create the incisions 186, as well as the incision for making the flap 180, without coagulating any or substantially any of the corneal tissue. Rather, the lasers cause a series of microexplosions to occur in the cornea 103, which create the incision without any coagulation. The flap 180 can then be allowed to relax back upon the exposed surface 181 and the remainder of the cornea 103 to assume a curvature as modified by the incisions 186. The other steps of washing the flap 180 and exposed surface 181, as well as applying the antibiotic drops and so on, can then be performed as described above.

The depths of the additional incisions 186 made under the flap 180 can have dimensions sufficient the correct the degree of hyperopia or presbyopia that is being experienced by the eye. In addition, the cutting blade that can be used to form the additional incision 186 underneath the flap 180 can be flexible so that it bows when force is applied to therefore create the incision 186 as a curved incision in the cornea underneath the flap 180. Furthermore, this additional incision or incisions can be made in the underside of the flap portion 180, if desired.

Figure 11:
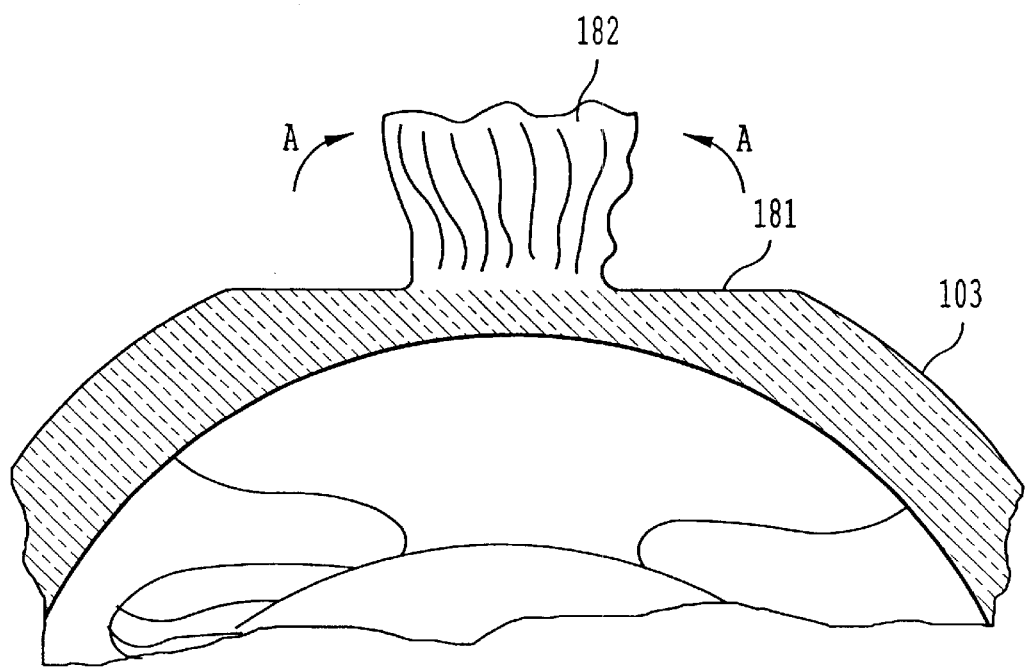
FIG. 11 is a cross-sectional view of the eye shown in FIG. 6 having a flap formed therein as shown in FIG. 9, which has been lifted up.
Figure 12:
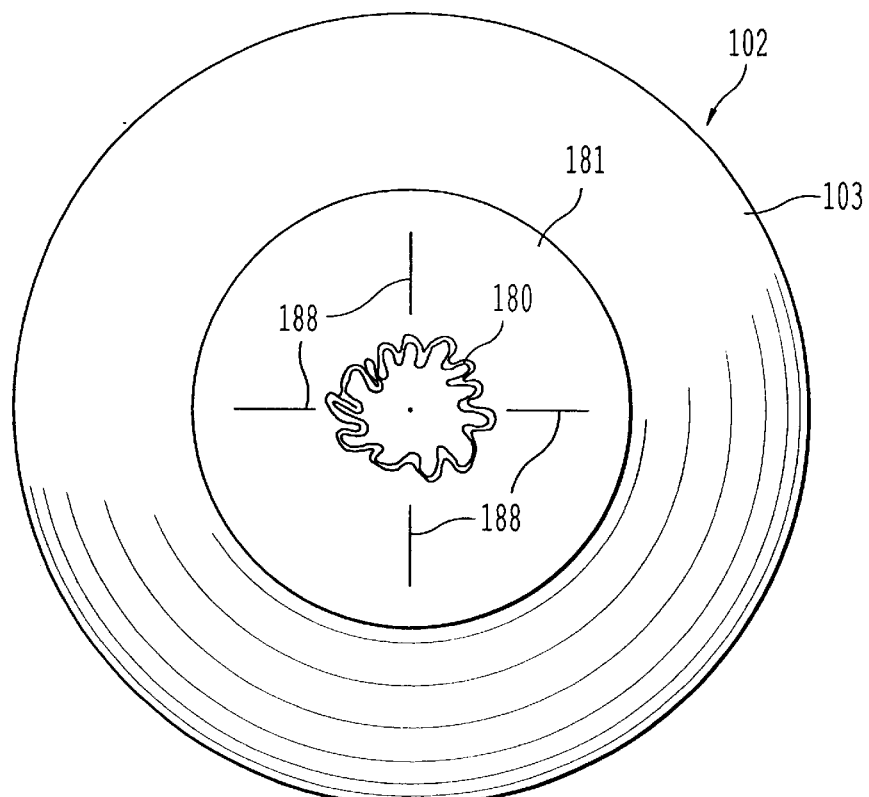
FIG. 12 is a top view of the eye as shown in FIG. 10, with additional incisions made in the exposed surface under the flap.
Figure 13:
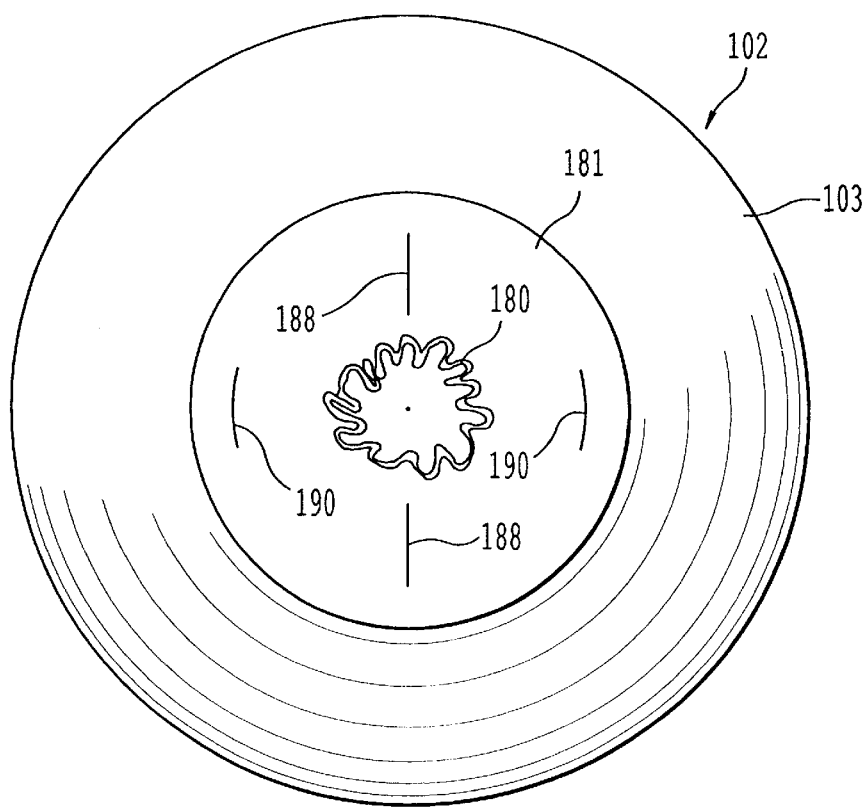
FIG. 13 is a top view of the eye as shown in FIG. 10, with additional incisions made in the exposed surface under the flap.
Figure 14:
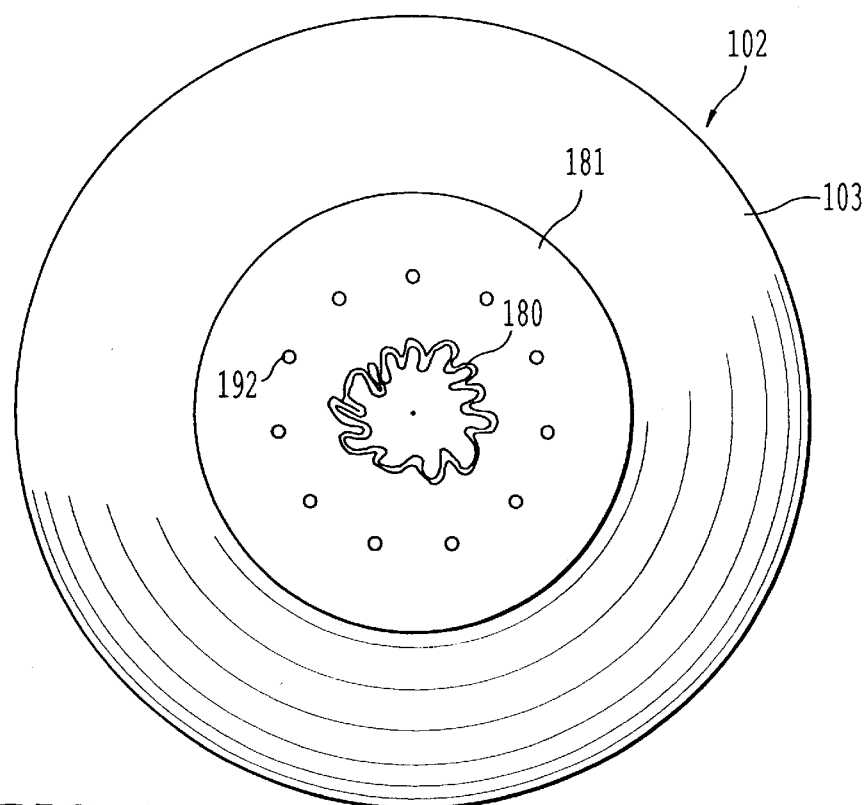
FIG. 14 is a top view of the eye as shown in FIG. 10, with tissue shrinkage produced in the exposed surface under the flap.

It is also noted that the cutting tools described above for making incision 186 can be used to create other types of incisions underneath the flap 180. For example, as shown in FIG. 11, the flap 180 can be lifted to expose most or all of the exposed surface 181. As shown in FIG. 12, one or more radial incisions 188 can be made in the surface of the cornea 103 underneath the flap 180 to correct for vision disorders such as myopia. It is noted that the radial incisions 188 are made without removing any or substantially any of the tissue from the exposed surface 181. Furthermore, as shown in FIG. 13, one or more radial incisions 188 can be made in the cornea underneath the flap 180, along with one or more actuate incisions 190, which correct astigmatism. As with the radial incisions 188, the actuate incisions 190 are formed without removing any or substantially any tissue from the exposed surface 181. Also. the lengths and depths of the radial and actuate incisions can vary as necessary to correct the degree of the vision disorder, and can be as deep as 95% of the remaining cornea 103.

As further shown in FIG. 13, tissue shrinkage areas 192 can be produced on the exposed surface 181 using tools such as a diathermy device, microwave emitting device, or a laser such as a contact (fiber optic) laser or a non-contact laser having nano-second ($10^{-9}$), pico-second ($10^{-12}$) or femto-second ($10^{-15}$) pulses. It is noted that these devices create the shrinkage areas 192 without causing any or substantially any ablation of the tissue, and without removing any or substantially any of the tissue. The shrinkage areas 192 can be circular, oval, or any other suitable shape to correct the vision disorder. It is noted that generally, radial incisions 188, such as those shown in FIG. 11 are formed to correct myopia, while actuate incisions 190 such as those shown in FIG. 12 are formed to correct astigmatism, and the shrinkage areas 192 are generally formed to correct hyperopia or presbyopia.

Figure 15:
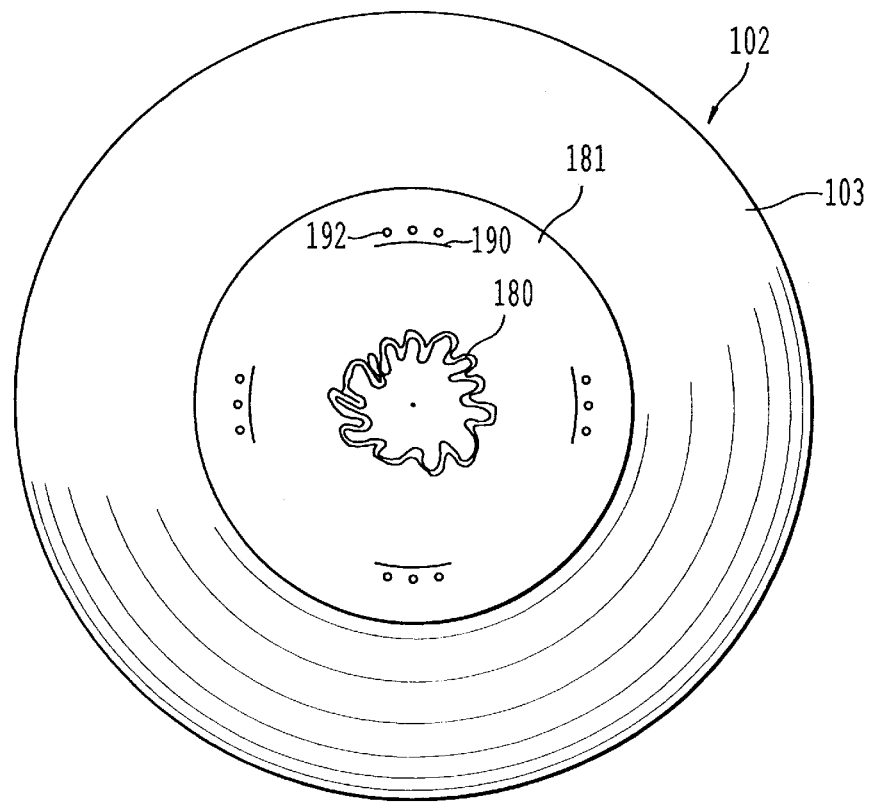
FIG. 15 is a top view of the eye as shown in FIG. 10, with the combination of incisions and tissue shrinkage made in the exposed surface under the flap.
Figure 16:
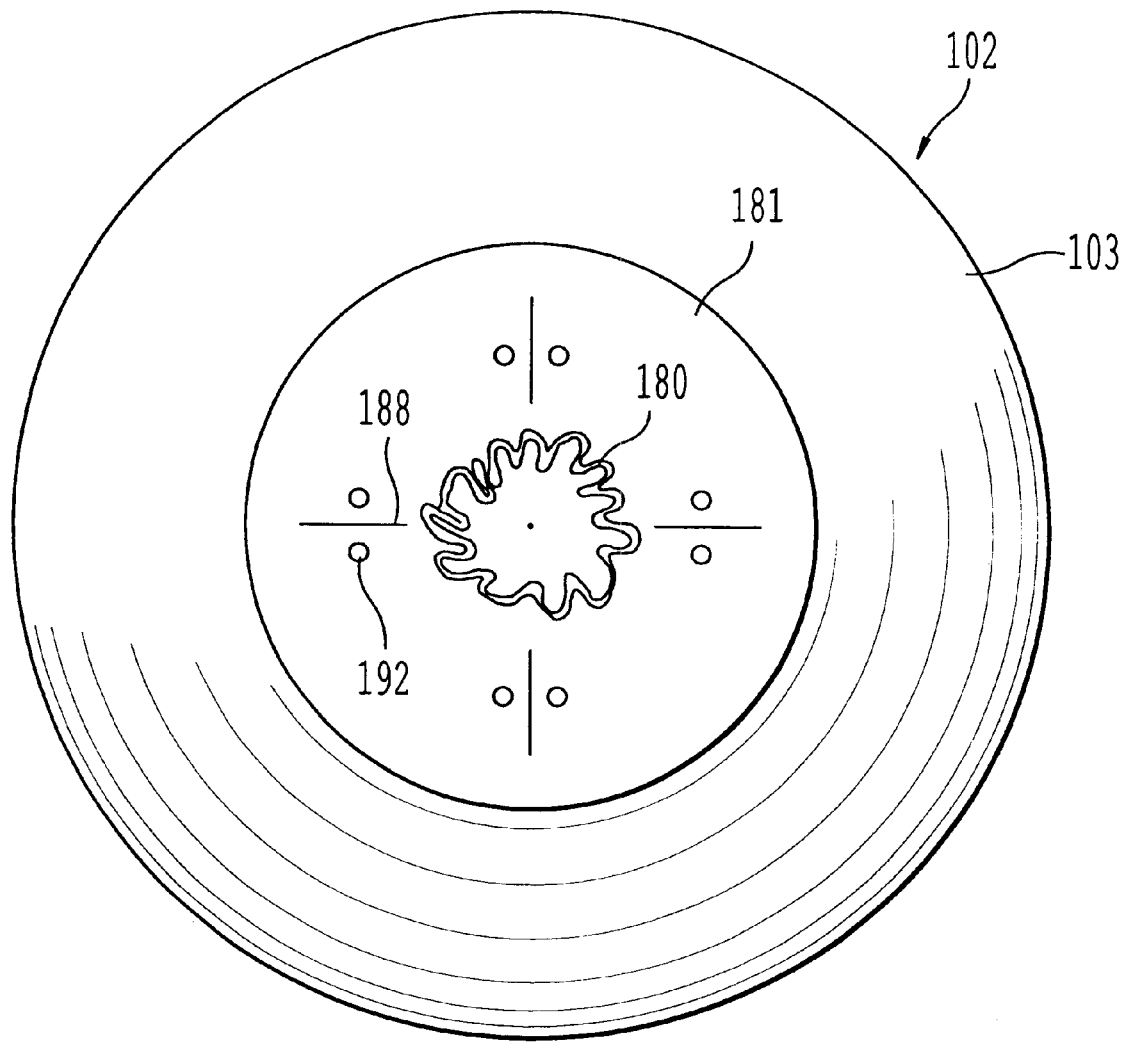
FIG. 16 is a top view of the eye as shown in FIG. 10, with the combination of incisions and tissue shrinkage made in the exposed surface under the flap.

Also, as further shown in FIGS. 15 and 16, the radial incisions 188, actuate incisions 190 and shrinkage areas 192 can be made in any combination and in any amount as appropriate to correct the vision disorder. They can also be made in addition to the incisions 186 (see FIG. 10), if desired. It is noted that the shrinkage areas 192, when formed adjacent to the incisions 188 or 190, can open the incisions 188 and 190, to provide for a further correction of the myopic or astigmatic condition.

In addition, although the above discussion relates to a peripheral flap 180. the tools described above can be used to form a full flap, such as that used for the LASIK procedure as described above, or a pocket type flap as described in U.S.

Pat. No. 5,964,776 cited above. The incisions 186, 188 and 190, as well as the shrinkage areas 192, can then be formed under the full flap or under the pocket type flap. Furthermore, if desired, any of the incisions or shrinkage areas can be formed in the bottom side of the flap 180, or on the bottom side of the pocket type flap or full flap, instead of or in addition to those formed on the exposed surface 181.

Figure 17:
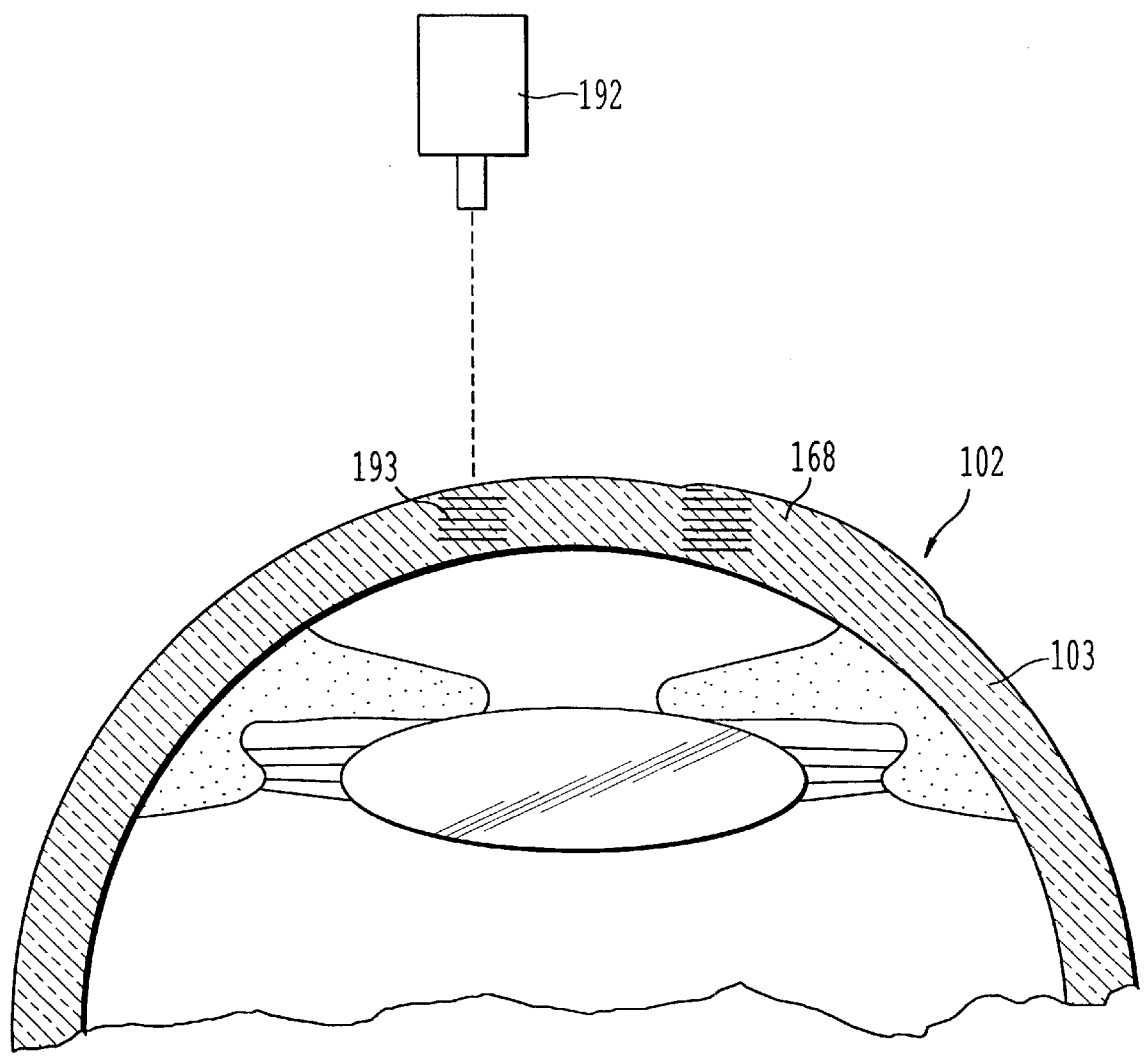
FIG. 17 is a cross-sectional view of the eye as shown in FIG. 6, with incisions made in the cornea prior to creation of the flap.
Figure 18:
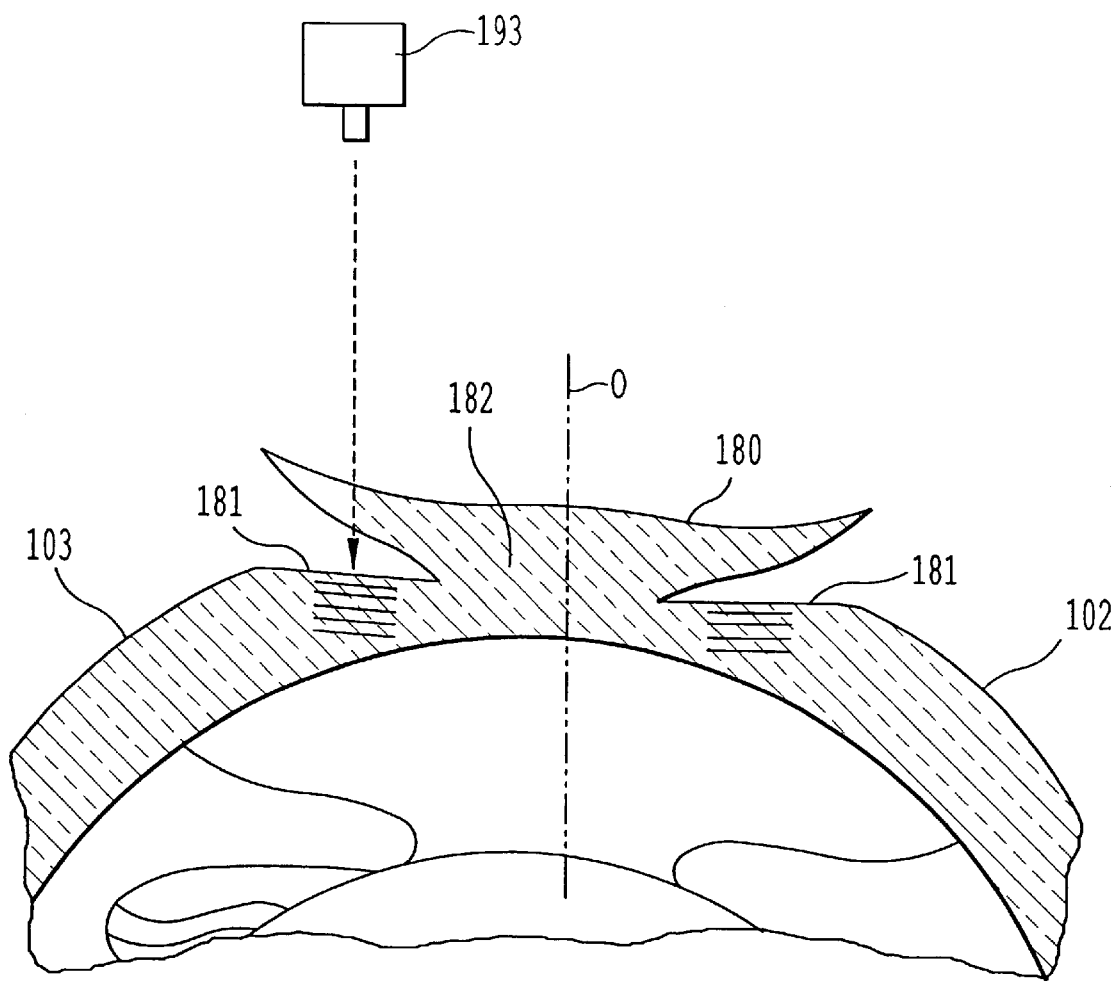
FIG. 18 is a cross-sectional view of the eye as shown in FIG. 6, with incisions made in the cornea after to creation of the flap.
Figure 19:
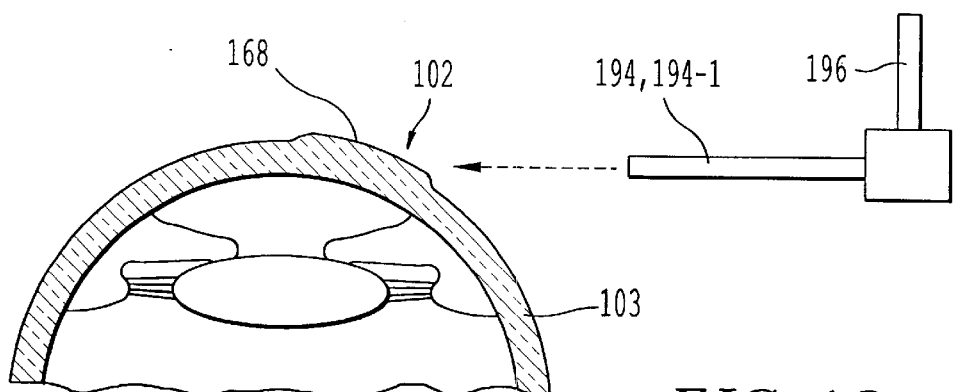
FIG. 19 is a side view of an eye used with a flap creating apparatus according to another embodiment of the present invention.
Figure 20:
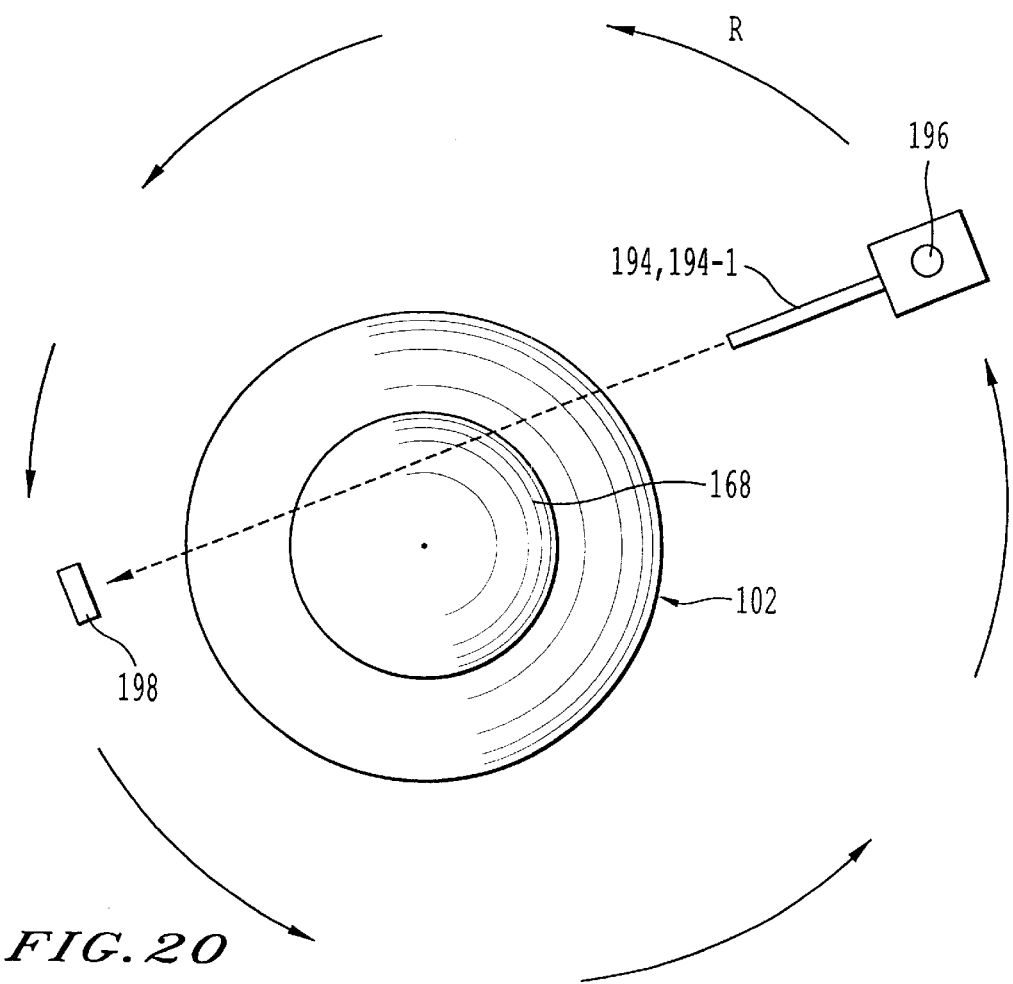
FIG. 20 is a top view of the eye and flap creating apparatus shown in FIG. 19.

Furthermore, as shown in FIGS. 17 and 18, a laser 193, such as an Nd-YAG laser, can be used to form incisions 193 at desired depths in the stroma of the cornea 103 prior to forming the flap 180 or after forming the flap 180. The laser 193 can be a contact laser or non-contact laser pulsed at nano, pico or femto second pulses, as described above, to form the incisions 193. Also, although FIGS. 17 and 18 show the incisions 193 as being formed prior to or after creation of a peripheral flap 180, the incisions can be formed before or after a full flap, such as that used for the LASIK procedure as described above, or a pocket type flap as described in U.S. Pat. No. 5,964,776 cited above.

Although the above description is related to apparatus 100 shown in FIGS. 1 through 5, it is also noted that other tools such a water-jet or laser can be used to make the incision in the cornea 103 that forms the flap 180. For example, as shown in FIGS. 17 and 18, a cornea holding apparatus (not shown), which can be similar to cornea holding apparatus 104, can be used in conjunction with a cutting apparatus 194, such as a water-jet or a laser. Assuming, for example, that the cutting apparatus is a water-jet, a support 196 of the cutting apparatus 194 positions the cutting apparatus 194 such that the water stream from the water-jet is directed perpendicular or substantially perpendicular to the optical axis O of the eye 102 in a horizontal or substantially horizontal direction toward the cornea 103, so that the water stream cuts the cornea 103 tangential toward the point of contact in a manner similar to blade 160 discussed above. The support 196 can be moved manually or by a driving mechanism (not shown) along a circular track (not shown), for example, to rotate the water-jet cutting apparatus 194 about the cornea 103 along the direction R shown in FIG. 18, while keeping the water stream horizontal or substantially horizontal with respect to the surface of the cornea 103, to form a flap 180 about the circumference of the cornea 103 in a manner as described above with regard to blade 160. A guard plate 198 also can be positioned to rotate along the circular track to follow the movement of the water jet and thus block the water jet.

As explained above, the incision forming the flap 180 can be made about the entire circumference of the cornea 103, only in an astigmatic portion 178 of the cornea 103, or at any other portion of the cornea 103. The flap 180 can therefore be allowed to relax on the cornea to correct the astigmatic condition in a manner as described above. Also, additional incisions such as those described with regard to FIGS. 9 through 16 can also be made underneath the flap 180 with the appropriate tools as discussed above.

Similarly, if the cutting tool 194 is a laser, such as those described above, the supporting apparatus 196 directs the laser beam in a direction perpendicular or substantially perpendicular to the optical axis O of the eye 103, and horizontal or substantially horizontal to the cornea 103, and rotates the laser cutting tool 202 about the cornea to form a flap 180 in a manner described above. It is noted that the laser beam has an intensity and wavelength to form the incision in the cornea without coagulating or substantially coagulating the tissue of the cornea 103. Rather, the incision is formed by a series of microexplosions that occur adjacent to each other in the cornea.

It is further noted that the cutting tool can be a laser water-jet 194-1 such as that manufactured by Visijet Company can be used to create the incision for the flap 180. This type of laser water-jet, or the water jet described above, can also be used to remove the lens cortex and nucleus, to remove a clot in an artery or vein, to remove cholesterol plaque in the coronary artery, and so on.

Figure 21:
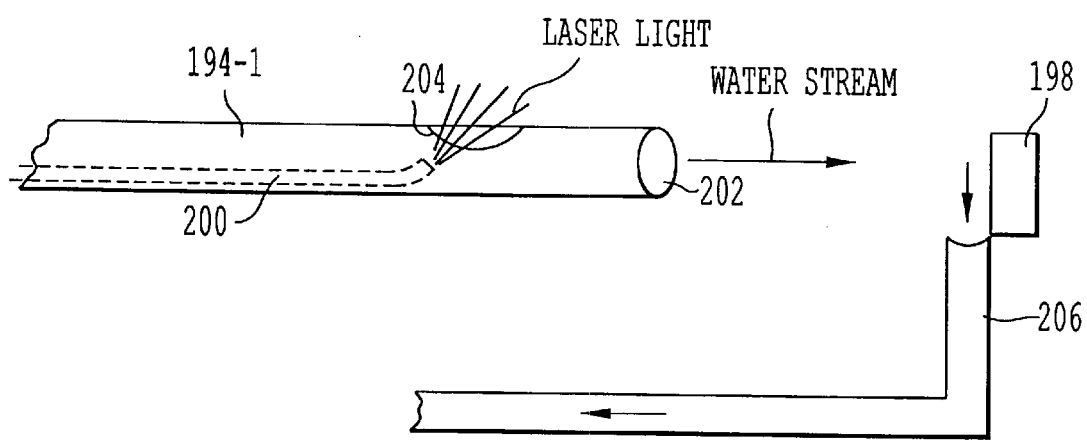
FIG. 21 is a schematic illustration of a laser water jet used as the flap creating apparatus as shown in FIGS. 19 and 20 according to an embodiment of the present invention.

As shown in FIG. 21, the laser water-jet 194-1 includes a water-jet instrument, such as those described above, along with a fiber optic cable 200 positioned to emit laser light into the water-jet tube. The laser light can be infrared, visible, ultraviolet or any other wavelength. The water stream can act as a conduit for the laser light, so that the laser light aids in forming the incision that forms the flap 180 as described above. The water jet and laser light can be emitted from the opening 202 in the end, or from the side opening 204, or both. For example, the side opening 204 can be blocked so that the water jet and laser light only passes through end 202, or the end 202 can be blocked so that the water stream and laser light only passes out of side opening 204. In addition, the guard plate 198 include a conduit 206 can be used to remove the water, be ejected from the laser water-jet 194-1.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for modifying a live cornea of an eye to correct a vision disorder in the eye, comprising:
   a cornea stabilizing device, adapted to retain the live cornea in a substantially stable position; and
   a cutting device, adapted to cut an incision about a least a portion of the circumference of the live cornea when said live cornea is being retained by said cornea stabilizing device, substantially without ablating said live cornea and substantially without removing any of said live cornea, to create a flap that is separable from a remaining portion of said live cornea, said flap remaining attached to said live cornea at an area through which the optical axis of said eye passes.

2. A system as claimed in claim 1, wherein:
   said cutting device comprises one of a blade, a water stream emitting device and a laser.

3. A system as claimed in claim 1, further comprising:
   a second cutting device, adapted to create at least one incision in said cornea at a surface of said cornea underneath said flap, substantially without ablating said live cornea and substantially without removing any of said live cornea.

4. A system as claimed in claim 3, wherein:
   said second cutting device is adapted to create said at least one incision as an incision that extends in a direction radially of the cornea.

5. A system as claimed in claim 3, wherein:
   said second cutting device is adapted to create said at least one incision as an arcuately-shaped incision.

6. A system as claimed in claim 3, wherein said cutting device and said second cutting device are the same device.

7. A system as claimed in claim 3, wherein said second cutting device comprises one of a blade, a water stream emitting device and a laser.

8. A system as claimed in claim 1, further comprising: an energy emitting device, adapted to generate shrinkage of at least a portion of said cornea under said flap.

9. A system as claimed in claim 8, wherein:

said energy emitting device comprises one of a laser, a microwave device and a diathermy device.

10. A method for modifying a live cornea of an eye to correct a vision disorder in the eye, comprising the steps of:

retaining the live cornea in a substantially stable position; and cutting an incision about a least a portion of the circumference of the live cornea when said live cornea is being retained, substantially without ablating said live cornea and substantially without removing any of said live cornea, to create a flap that is separable from a remaining portion of said live cornea, said flap remaining attached to said live cornea at an area through which the optical axis of said eye passes.

11. A method as claimed in claim 10, wherein:

said cutting step uses at least one of a blade, a water stream emitting device and a laser to form said incision.

12. A method as claimed in claim 10, further comprising the steps of:

creating at least one incision in said cornea at a surface of said cornea underneath said flap, substantially without ablating said live cornea and substantially without removing any of said live cornea.

13. A method as claimed in claim 12, wherein:

said creating step creates said at least one incision as an incision that extends in a direction radially of the cornea.

14. A method as claimed in claim 12, wherein:

said creating step creates said at least one incision as an arcuately-shaped incision.

15. A method as claimed in claim 12, wherein said cutting step and said creating step use the same cutting device.

16. A method as claimed in claim 12, wherein said creating step uses at least one of a blade, a water stream emitting device and a laser.

17. A method as claimed in claim 10, further comprising the step of:

emitting energy toward at least a portion of said cornea under said flap to generate shrinkage of said at least a portion of said cornea under said flap.

18. A method as claimed in claim 17, wherein:

said energy emitting step uses at least one of a laser, a microwave device and a diathermy device.

19. A system for modifying a live cornea of an eye to correct a vision disorder in the eye, comprising:

a cornea stabilizing device, adapted to retain the live cornea in a substantially stable position; and a cutting device, adapted to cut an incision in the live cornea when said live cornea is being retained by said cornea stabilizing device, substantially without ablating said live cornea and substantially without removing any of said live cornea, to create a flap that is separable from a remaining portion of said live cornea; and at least one of the following:

a second cutting device, adapted to create at least one incision in said cornea at a surface of said cornea underneath said flap, substantially without ablating said live cornea and substantially without removing any of said live cornea; and an energy emitting device, adapted to generate shrinkage of at least a portion of said cornea under said flap.

20. A method for modifying a live cornea of an eye to correct a vision disorder in the eye, comprising the steps of:

retaining the live cornea in a substantially stable position; and cutting an incision in the live cornea when said live cornea is being retained by said cornea stabilizing device, substantially without ablating said live cornea and substantially without removing any of said live cornea, to create a flap that is separable from a remaining portion of said live cornea; and performing at least one of the following steps:

creating at least one incision in said cornea at a surface of said cornea underneath said flap, substantially without ablating said live cornea and substantially without removing any of said live cornea; and emitting energy toward at least a portion of said cornea underneath said flap to generate shrinkage of said at least a portion of said cornea under said flap.

\* \* \* \* \*